United States Patent [19]
Bouchard et al.

[11] Patent Number: 5,968,931
[45] Date of Patent: Oct. 19, 1999

[54] TAXOIDS, PREPARATION THEREOF AND PHARMACEUTICAL COMPOSITIONS CONTAINING SAME

[75] Inventors: Hervé Bouchard, Thais; Alain Commerçon, Vitry-sur-Seine, both of France

[73] Assignee: Rhone-Poulenc Rorer S.A., Antony, France

[21] Appl. No.: 09/091,188

[22] PCT Filed: Dec. 19, 1996

[86] PCT No.: PCT/FR96/02030

§ 371 Date: Jun. 10, 1998

§ 102(e) Date: Jun. 10, 1998

[87] PCT Pub. No.: WO97/23472

PCT Pub. Date: Jul. 3, 1997

[30] Foreign Application Priority Data

Dec. 22, 1995 [FR] France .................................. 95 15380

[51] Int. Cl.⁶ ...................... A61K 31/335; A61K 31/395; C07D 305/14; C07D 405/02
[52] U.S. Cl. .................................... 514/226.8; 514/227.8; 514/231.5; 514/255; 514/320; 514/444; 514/449; 514/461; 544/106; 544/359; 546/196; 548/146; 548/206; 549/60; 549/472; 549/511
[58] Field of Search ............................... 549/511, 60, 472; 514/226.8, 227.8, 231.5, 255, 320, 444, 449, 461; 544/106, 359; 548/146, 206

[56] References Cited

U.S. PATENT DOCUMENTS

| | | |
|---|---|---|
| 5,380,751 | 1/1995 | Chen et al. . |
| 5,532,388 | 7/1996 | Bouchard et al. . |
| 5,550,261 | 8/1996 | Bouchard et al. . |
| 5,571,917 | 11/1996 | Bouchard et al. . |
| 5,576,450 | 11/1996 | Bouchard et al. . |
| 5,580,997 | 12/1996 | Bouchard et al. . |
| 5,580,998 | 12/1996 | Bouchard et al. . |
| 5,587,483 | 12/1996 | Johnson et al. . |

FOREIGN PATENT DOCUMENTS

0600517A1  6/1994  European Pat. Off. .

*Primary Examiner*—Johann Richter
*Assistant Examiner*—Taofiq A. Solola
*Attorney, Agent, or Firm*—Finnegan, Henderson, Farabow, Garrett & Dunner, L.L.P.

[57] ABSTRACT

Novel taxoids of general formula (I), the preparation thereof, and pharmaceutical compositions containing the novel taxoids:

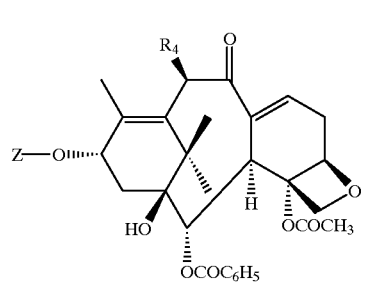

(I)

wherein Z represents a hydrogen atom or a radical of general formula (II):

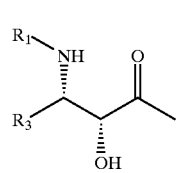

(II)

15 Claims, No Drawings

TAXOIDS, PREPARATION THEREOF AND PHARMACEUTICAL COMPOSITIONS CONTAINING SAME

This application is a 371 of a PCT/FR96/02030 filed Dec. 19, 1996.

The present invention relates to new taxoids of general formula:

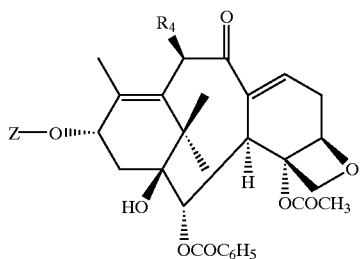

(I)

in which:

Z represents a hydrogen atom or a radical of general formula:

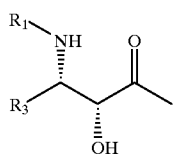

(II)

in which:

$R_1$ represents a benzoyl radical optionally substituted with one or more identical or different atoms or radicals chosen from halogen atoms and alkyl radicals containing 1 to 4 carbon atoms, alkoxy radicals containing 1 to 4 carbon atoms or trifluoromethyl radicals, a thenoyl or furoyl radical or a radical $R_2$—O—CO— in which $R_2$ represents:

an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with one or more substituents chosen from halogen atoms and hydroxyl radicals, alkoxy radicals containing 1 to 4 carbon atoms, dialkylamino radicals in which each alkyl portion contains 1 to 4 carbon atoms, piperidino or morpholino radicals, 1-piperazinyl radicals (optionally substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl radicals (optionally substituted with one or more atoms or radicals chosen from halogen atoms and alkyl radicals containing 1 to 4 carbon atoms or alkoxy radicals containing 1 to 4 carbon atoms), cyano or carboxyl radicals or alkoxycarbonyl radicals in which the alkyl portion contains 1 to 4 carbon atoms, a phenyl or α- or β-naphthyl radical optionally substituted with one or more atoms or radicals chosen from halogen atoms and alkyl radicals containing 1 to 4 carbon atoms or alkoxy radicals containing 1 to 4 carbon atoms, or a 5-membered aromatic heterocyclic radical preferably chosen from furyl and thienyl radicals, or a saturated heterocyclic radical containing 4 to 6 carbon atoms, optionally substituted with one or more alkyl radicals containing 1 to 4 carbon atoms, $R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical optionally substituted with one or more atoms or radicals chosen from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more identical or different hetero atoms chosen from nitrogen, oxygen and sulphur atoms and optionally substituted with one or more identical or different substituents chosen from halogen atoms and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl or alkoxycarbonyl radicals, on the understanding that, in the substituents of the phenyl, α- or β-naphthyl and aromatic heterocyclic radicals, the alkyl radicals and the alkyl portions of the other radicals contain 1 to 4 carbon atoms, and that the alkenyl and alkynyl radicals contain 2 to 8 carbon atoms, and that the aryl radicals are phenyl or α- or β-naphthyl radicals, $R_4$ represents a hydrogen atom or a hydroxyl radical or an alkoxy radical containing 1 to 6 carbon atoms in an unbranched or branched chain, an alkenyloxy radical containing 3 to 6 carbon atoms in an unbranched or branched chain, an alkynyloxy radical containing 3 to 6 carbon atoms in an unbranched or branched chain, a cycloalkyloxy radical containing 3 to 6 carbon atoms, a cycloalkenyloxy radical containing 3 to 6 carbon atoms, an alkanoyloxy radical in which the alkanoyl portion contains 1 to 6 carbon atoms in an unbranched or branched chain, an alkenoyloxy radical in which the alkenoyl portion contains 3 to 6 carbon atoms in an unbranched or branched chain, an alkynoyloxy radical in which the alkynoyl portion contains 3 to 6 carbon atoms in an unbranched or branched chain, a cycloalkanoyloxy radical containing 1 to 6 carbon atoms, an alkoxyacetyl radical in which the alkyl portion contains 1 to 6 carbon atoms in an unbranched or branched chain, an alkylthioacetyl radical in which the alkyl portion contains 1 to 6 carbon atoms in an unbranched or branched chain or an alkyloxycarbonyloxy radical in which the alkyl portion contains 1 to 6 carbon atoms in an unbranched or branched chain, these radicals being optionally substituted with one or more halogen atoms or with an alkoxy radical containing 1 to 4 carbon atoms, an alkylthio radical containing 1 to 4 carbon atoms or a carboxyl radical, an alkyloxycarbonyl radical in which the alkyl portion contains 1 to 4 carbon atoms, a cyano or carbamoyl radical or an N-alkylcarbamoyl or N,N-dialkylcarbamoyl radical in which each alkyl portion contains 1 to 4 carbon atoms or, with the nitrogen atom to which it is linked, forms a saturated 5- or 6-membered heterocyclic radical optionally containing a second hetero atom chosen from oxygen, sulphur and nitrogen atoms, optionally substituted with an alkyl radical containing 1 to 4 carbon atoms or a phenyl radical or a phenylalkyl radical in which the alkyl portion contains 1 to 4 carbon atoms, or alternatively $R_4$ represents a carbamoyloxy radical, an alkoxycarbamoyloxy radical in which the alkyl portion contains 1 to 4 carbon atoms, a dialkylcarbamoyloxy radical in which each alkyl portion contains 1 to 4 carbon atoms, a benzoyloxy radical or a heterocyclic radical attached to a carbonyloxy group in which radical the heterocyclic portion represents a 5- or 6-membered aromatic heterocycle containing one or more hetero atoms chosen from oxygen, sulphur and nitrogen atoms.

Preferably, the aryl radicals which can be represented by $R_3$ are phenyl or α- or β-naphthyl radicals optionally substituted with one or more atoms or radicals chosen from halogen atoms (fluorine, chlorine, bromine, iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, on the understanding that the alkyl radicals and the alkyl portions of the other radicals contain 1 to 4 carbon atoms, that the alkenyl and alkynyl radicals contain 2 to 8 carbon atoms and that the aryl radicals are phenyl or α- or β-naphthyl radicals.

Preferably, the heterocyclic radicals which can be represented by $R_3$ are 5-membered aromatic heterocyclic radicals containing one or more identical or different atoms chosen from nitrogen, oxygen and sulphur atoms, optionally substituted with one or more identical or different substituents chosen from halogen atoms (fluorine, chlorine, bromine, iodine) and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, dialkylamino radicals in which each alkyl portion contains 1 to 4 carbon atoms, acylamino radicals in which the acyl portion contains 1 to 4 carbon atoms, alkoxycarbonylamino radicals containing 1 to 4 carbon atoms, acyl radicals containing 1 to 4 carbon atoms, arylcarbonyl radicals in which the aryl portion contains 6 to 10 carbon atoms, cyano, carboxyl or carbamoyl radicals, alkylcarbamoyl radicals in which the alkyl portion contains 1 to 4 carbon atoms, dialkylcarbamoyl radicals in which each alkyl portion contains 1 to 4 carbon atoms or alkoxycarbonyl radicals in which the alkoxy portion contains 1 to 4 carbon atoms.

Preferably, the radical $R_4$ represents a hydroxyl radical or an unbranched or branched alkoxy radicals containing 1 to 6 carbon atoms or an alkenoyloxy radical containing 1 to 6 carbon atoms, optionally substituted with a methoxy, ethoxy, methylthio ethylthio radical or a carboxyl, methoxycarbonyl, ethoxycarbonyl, cyano, carbamoyl, N-methylcarbamoyl, N-ethylcarbamoyl, N,N-dimethylcarbamoyl, N,N-diethylcarbamoyl, N-pyrrolidinocarbonyl or N-piperidinocarbonyl radical.

More especially, the present invention relates to the products of general formula (I) in which Z represents a hydrogen atom or a radical of general formula (II) in which $R_1$ represents a benzoyl radical or a radical $R_2$—O—CO— in which $R_2$ represents a tert-butyl radical and $R_3$ represents an alkyl radical containing 1 to 6 carbon atoms, an alkenyl radical containing 2 to 6 carbon atoms, a cycloalkyl radical containing 3 to 6 carbon atoms, a phenyl radical optionally substituted with one or more identical or different atoms or radicals chosen from halogen atoms (fluorine, chlorine) and alkyl (methyl), alkoxy (methoxy), dialkylamino (dimethylamino), acylamino (acetylamino), alkoxycarbonylamino (tert-butoxycarbonylamino) or trifluoromethyl radicals, or a 2- or 3-furyl, 2- or 3-thienyl or 2-, 4- or 5-thiazolyl radical, and $R_4$ represents a hydroxyl radical or an unbranched or branched alkyloxy radical containing 1 to 6 carbon atoms or an alkanoyloxy radical containing 1 to 6 carbon atoms.

Still more especially, the present invention relates to the products of general formula (I) in which Z represents a hydrogen atom or a radical of general formula (II) in which $R_1$ represents a benzoyl radical or a radical $R_2$—O—CO— in which $R_2$ represents a tert-butyl radical and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical, and $R_4$ represents a hydroxyl, methoxy or acetoxy radical.

The products of general formula (I) in which Z represents a radical of general formula (II) display noteworthy antitumour and antileukaemic properties.

According to the invention, the products of general formula (I) may be obtained by heating, in the presence of an activating agent such as an alkali metal halide (sodium chloride) or an alkali metal azide (sodium azide) or an ammonium salt or of silica, a product of general formula:

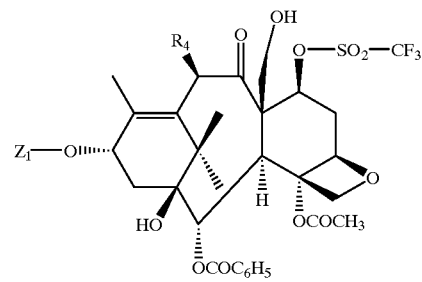

(III)

in which $R_4$ is defined as above and $Z_1$ represents a hydrogen atom or a radical of general formula:

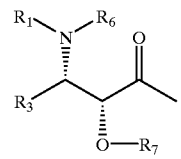

(IV)

in which either $R_6$ represents a hydrogen atom and $R_7$ represents a hydrogen atom or a group protecting the hydroxyl function, or $R_6$ and $R_7$ together form a saturated 5- or 6-membered heterocycle, to obtain a product of general formula:

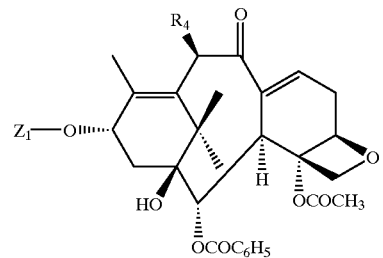

(V)

in which $Z_1$ and $R_4$ are defined as above, followed where appropriate by replacement of the protective groups by hydrogen atoms.

Generally, the elimination reaction is performed working in an organic solvent chosen from ethers (tetrahydrofuran, diisopropyl ether, methyl t-butyl ether), nitriles (acetonitrile), halogenated aliphatic hydrocarbons (dichloroethane) or aliphatic esters (ethyl acetate), taken alone or mixed, at a temperature between 20° C. and the refluxing temperature of the reaction mixture.

Preferably, $R_6$ represents a hydrogen atom and $R_7$ represents a group protecting the hydroxyl function, or alternatively $R_6$ and $R_7$ together form a saturated 5- or 6-membered heterocycle.

When $R_6$ represents a hydrogen atom, $R_7$ preferably represents a methoxymethyl, 1-ethoxyethyl, benzyloxymethyl, trimethylsilyl, triethylsilyl, β-trimethylsilylethoxymethyl, benzyloxycarbonyl or tetrahydropyranyl radical.

When $R_6$ and $R_7$ together form a heterocycle, the latter is preferably an oxazolidine ring optionally monosubstituted or gem-disubstituted at position 2.

Replacement of the protective groups $R_7$ and/or $R_6$ and $R_7$ by hydrogen atoms may be performed, depending on their nature, in the following manner:

1) when $R_6$ represents a hydrogen atom and $R_7$ represents a group protecting the hydroxyl function, replacement of the protective groups by hydrogen atoms is performed by means of an inorganic acid (hydrochloric acid, sulphuric acid, hydrofluoric acid) or organic acid (acetic acid, methanesulphonic acid, trifluoromethanesulphonic acid, p-toluenesulphonic acid) used alone or mixed, working in an organic solvent chosen from alcohols, ethers, esters, aliphatic hydrocarbons, halogenated aliphatic hydrocarbons, aromatic hydrocarbons or nitriles at a temperature of between −10 and 60° C., or by means of a source of fluoride ions such as a hydrofluorine acid/triethylamine complex, or by catalytic hydrogenation, 2) when $R_6$ and $R_7$ together form a saturated 5- or 6-membered heterocycle, and more especially an oxazolidine ring of general formula:

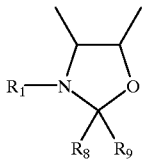

(VI)

in which $R_1$ is defined as above and $R_8$ and $R_9$, which may be identical or different, represent a hydrogen atom or an alkyl radical containing 1 to 4 carbon atoms, or an aralkyl radical in which the alkyl portion contains 1 to 4 carbon atoms and the aryl portion preferably represents a phenyl radical optionally substituted with one or more alkoxy radicals containing 1 to 4 carbon atoms, or an aryl radical preferably representing a phenyl radical optionally substituted with one or more alkoxy radicals containing 1 to 4 carbon atoms, or alternatively $R_8$ represents an alkoxy radical containing 1 to 4 carbon atoms or a trihalomethyl radical such as trichloromethyl or a phenyl radical substituted with a trihalomethyl radical such as trichloromethyl and $R_9$ represents a hydrogen atom, or alternatively $R_8$ and $R_9$, together with the carbon atom to which they are linked, form a 4- to 7-membered ring, replacement of the protective group formed by $R_6$ and $R_7$ by hydrogen atoms may be performed, depending on the meanings of $R_1$, $R_8$ and $R_9$, in the following manner:

a) when $R_1$ represents a tert-butoxycarbonyl radical and $R_8$ and $R_9$, which may be identical or different, represent an alkyl radical or an aralkyl (benzyl) or aryl (phenyl) radical, or alternatively $R_8$ represents a trihalomethyl radical or a phenyl radical substituted with a trihalomethyl radical and $R_9$ represents a hydrogen atom, or alternatively $R_8$ and $R_9$ together form a 4- to 7-membered ring, treatment of the ester of general formula (V) with an inorganic or organic acid, where appropriate in an organic solvent such as an alcohol, yields the product of general formula:

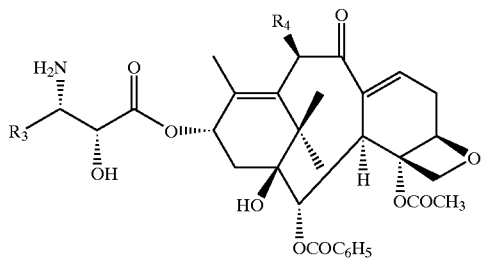

(VII)

in which $R_3$ and $R_4$ are defined as above, which is acylated by means of benzoyl chloride in which the phenyl ring is optionally substituted or by means of thenoyl chloride, of furoyl chloride or of a product of general formula:

$$R_2\text{—O—CO—X} \qquad \text{(VIII)}$$

in which $R_2$ is defined as above and X represents a halogen atom (fluorine, chlorine) or a residue —O—$R_2$ or —O—CO—O—$R_2$, to obtain a product of general formula (I) in which Z represents a radical of general formula (II).

Preferably, the product of general formula (V) is treated with formic acid at a temperature in the region of 20° C. to yield the product of general formula (VII).

Preferably, the acylation of the product of general formula (VII) by means of a benzoyl chloride in which the phenyl radical is optionally substituted or by means of thenoyl chloride, of furoyl chloride or of a product of general formula (VIII) is performed in an inert organic solvent chosen from esters such as ethyl acetate, isopropyl acetate or n-butyl acetate and halogenated aliphatic hydrocarbons such as dichloromethane or 1,2-dichloroethane, in the presence of an inorganic base such as sodium bicarbonate or an organic base such as triethylamine. The reaction is performed at a temperature of between 0 and 50° C., and preferably in the region of 20° C.

b) when $R_1$ represents an optionally substituted benzoyl radical, a thenoyl or furoyl radical or a radical $R_2$O—CO— in which $R_2$ is defined as above, $R_8$ represents a hydrogen atom or an alkoxy radical containing 1 to 4 carbon atoms or a phenyl radical substituted with one or more alkoxy radicals containing 1 to 4 carbon atoms and $R_9$ represents a hydrogen atom, replacement of the protective group formed by $R_6$ and $R_7$ by hydrogen atoms is performed in the presence of an inorganic acid (hydrochloric acid, sulphuric acid) or organic acid (acetic acid, methanesulphonic acid, trifluoromethanesulphonic acid, p-toluenesulphonic acid) used alone or mixed in a stoichiometric or catalytic amount, working in an organic solvent chosen from alcohols, ethers, esters, aliphatic hydrocarbons, halogenated aliphatic hydrocarbons and aromatic hydrocarbons at a temperature of between −10 and 60° C., and preferably between 15 and 30° C.

The product of general formula (III) in which $R_4$ represents a hydroxyl radical may be obtained by the action of a trifluoromethanesulphonic acid derivative such as the anhydride or N-phenyltrifluoromethanesulphonimide in an inert organic solvent such as an optionally halogenated aliphatic hydrocarbon, for instance dichloromethane, working in the presence of an organic base such as pyridine or a tertiary aliphatic amine such as triethylamine at a temperature of between −50 and 20° C., on a product of general formula:

(IX)

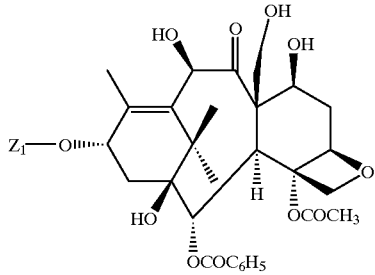

in which $Z_1$ is defined as above.

The product of general formula (IX) may be obtained from a product of general formula:

(X)

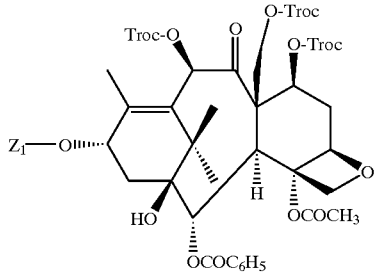

in which $Z_1$ is defined as above and Troc represents a 2,2,2-trichloroethoxycarbonyl radical, by the action of zinc optionally in combination with copper in the presence of acetic acid at a temperature of between 20 and 60° C., or by means of an inorganic or organic acid such as hydrochloric acid or acetic acid in solution in an aliphatic alcohol containing 1 to 3 carbon atoms or in an aliphatic ester such as ethyl acetate, isopropyl acetate or n-butylacetate in the presence of zinc, optionally in combination with copper.

The product of general formula (X) in which $Z_1$ represents a radical of general formula (IV) in which $R_1$ and $R_3$ are defined as above, and either $R_6$ represents a hydrogen atom and $R_7$ represents a group protecting the hydroxyl function, or $R_6$ and $R_7$ together form a saturated 5- or 6-membered heterocycle, may be obtained by esterification of the product of formula:

(XI)

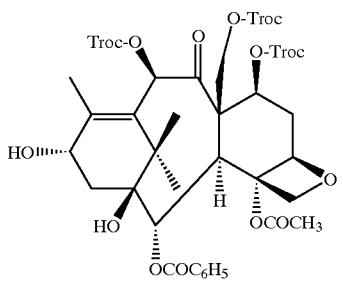

in which Troc is defined as above, by means of an acid or a derivative of this acid of general formula:

(XII)

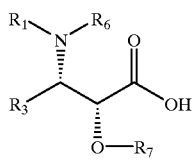

in which $R_1$ and $R_3$ are defined as above and $R_6$ and $R_7$ are defined as before.

The esterification by means of an acid of general formula (XII) may be performed in the presence of a condensing agent (carbodiimide, reactive carbonate) and an activating agent (aminopyridines) in an organic solvent (ether, ester, ketones, nitrites, aliphatic hydrocarbons, halogenated aliphatic hydrocarbons, aromatic hydrocarbons) at a temperature of between −10 and 90° C.

The esterification may also be carried out using the acid of general formula (XII) in the form of the symmetrical anhydride, working in the presence of an activating agent (aminopyridines) in an organic solvent (ethers, esters, ketones, nitriles, aliphatic hydrocarbons, halogenated aliphatic hydrocarbons, aromatic hydrocarbons) at a temperature of between 0 and 90° C.

The esterification may also be carried out using the acid of general formula (XII) in halide form or in the form of a mixed anhydride with an aliphatic or aromatic acid, optionally prepared in situ, in the presence of a base (tertiary aliphatic amine), working in an organic solvent (ethers, esters, ketones, nitriles, aliphatic hydrocarbons, halogenated aliphatic hydrocarbons, aromatic hydrocarbons) at a temperature of between 0 and 80° C.

The product of formula (XI) may be obtained under the conditions described in International Application PCT WO 94/01425.

The product of general formula (III) in which $R_4$ represents an alkoxy radical containing 1 to 6 carbon atoms in an unbranched or branched chain, an alkenyloxy radical containing 3 to 6 carbon atoms in an unbranched or branched chain, an alkynyloxy radical containing 3 to 6 carbon atoms in an unbranched or branched chain, a cycloalkyloxy radical containing 3 to 6 carbon atoms, a cycloalkenyloxy radical containing 3 to 6 carbon atoms, an alkanoyloxy radical in which the alkanoyl portion contains 1 to 6 carbon atoms in an unbranched or branched chain, an alkenoyloxy radical in which the alkenoyl portion contains 3 to 6 carbon atoms in an unbranched or branched chain, an alkynoyloxy radical in which the alkynoyl portion contains 3 to 6 carbon atoms in an unbranched or branched chain, a cycloalkanoyloxy radical containing 1 to 6 carbon atoms, an alkoxyacetyl radical in which the alkyl portion contains 1 to 6 carbon atoms in an unbranched or branched chain, an alkylthioacetyl radical in which the alkyl portion contains 1 to 6 carbon atoms in an unbranched or branched chain or an alkyloxycarbonyloxy radical in which the alkyl portion contains 1 to 6 carbon atoms in an unbranched or branched chain, these radicals being optionally substituted with one or more halogen atoms or with an alkoxy radical containing 1 to 4 carbon atoms, an alkylthio radical containing 1 to 4 carbon atoms or a carboxyl radical, an alkyloxycarbonyl radical in which the alkyl portion contains 1 to 4 carbon atoms, a cyano or carbamoyl radical or an N-alkylcarbamoyl or N,N-dialkylcarbamoyl radical in which each alkyl portion contains 1 to 4 carbon atoms or, with the nitrogen atom to which it is linked, forms a saturated 5- or 6-membered heterocyclic radical optionally containing a second hetero atom chosen from oxygen, sulphur and nitrogen atoms, optionally substituted with an alkyl radical containing 1 to 4 carbon atoms or a phenyl radical or a phenylalkyl radical in which the alkyl portion contains 1 to 4 carbon atoms, or alternatively $R_4$ represents a carbamoyloxy radical, an alkoxycarbamoyloxy radical in which the alkyl portion contains 1 to 4 carbon atoms, a dialkylcarbamoyloxy radical in which each alkyl portion contains 1 to 4 carbon atoms, a benzoyloxy radical or a heterocyclic radical attached to a carbonyloxy group in which radical the heterocyclic portion represents a 5- or 6-membered aromatic heterocycle containing one or more hetero atoms chosen from oxygen, sulphur and nitrogen atoms, and $Z_1$ is defined as above, may be obtained from a product of general formula (III) in which $Z_1$ is defined as above and $R_4$ represents a hydroxyl radical, by the action of a product of general formula:

$$R'_4\text{—}Y \quad \text{(XIII)}$$

in which $R'_4$ is such that $R'_4$—O— is identical to $R_4$ defined as above and Y represents a leaving group such as a halogen atom or an alkylsulphonyl or arylsulphonyl radical or, when $R'_4$ represents the residue of a carboxylic acid, such as an alkanoyloxy radical, a radical —O—$R'_4$.

Generally, the action of a product of general formula (XIII) on the product of general formula (III) defined before is performed, after possible metalization of the hydroxyl function at position 10 by means of an alkali metal hydride such as sodium hydride, an alkali metal amide such as lithium diisopropylamide or an alkali metal alkylide such as butyllithium, working in an organic solvent such as dimethylformamide or tetrahydrofuran at a temperature of between −30 and 50° C., followed where appropriate by replacement of the group protecting the hydroxyl function under the conditions described above.

The product of general formula (III) in which $R_4$ represents a hydrogen atom may be obtained from a product of general formula (III) in which $R_4$ represents a hydroxyl radical under the conditions described, for example, in International Applications PCT WO 93/06093 or WO 94/11547, or by conversion of the hydroxyl radical represented by $R_4$ to dithiocarbonate followed by reduction of the product obtained by means of a trialkyltin hydride, or alternatively by reduction in the presence of samarium iodide.

The new products of general formula (I) obtained by carrying out the processes according to the invention may be purified according to known methods such as crystallization or chromatography.

The products of general formula (I) in which Z represents a radical of general formula (II) display noteworthy biological properties.

In vitro, measurement of the biological activity is performed on tubulin extracted from pig's brain by the method of M. L. Shelanski et al., Proc. Natl. Acad. Sci. USA, 70, 765–768 (1973). Study of the depolymerization of microtubules to tubulin is performed according to the method of G. Chauvière et al., C.R. Acad. Sci., 293, series II, 501–503 (1981). In this study, the products of general formula (I) in which Z represents a radical of general formula (II) were shown to be at least as active as taxol and Taxotere.

In vivo, the products of general formula (I) in which Z represents a radical of general formula (II) were shown to be active in mice grafted with B16 melanoma at doses of between 1 and 10 mg/kg administered intraperitoneally, as well as on other liquid or solid tumours.

The new products have antitumour properties, and more especially activity against tumours which are resistant to Taxol® or to Taxotere®. Such tumours comprise colon tumours which have a high expression of the mdr 1 gene (multiple drug resistance gene). Multiple drug resistance is a customary term relating to the resistance of a tumour to different products having different structures and mechanisms of action. Taxoids are generally known to be strongly recognized by experimental tumours such as P388/DOX, a cell line selected for its resistance to doxorubicin (DOX) which expresses mdr 1.

The examples which follow illustrate the present invention.

EXAMPLE 1

A suspension, maintained under an argon atmosphere, of 120 mg of 4α,10β-diacetoxy-2α-benzoyloxy-5β,20-epoxy-1β,19-dihydroxy-9-oxo-7β-trifluoromethanesulphonyloxy-11-taxen-13α-yl (2R,3S)-3-tert-butoxycarbonylamino-2-hydroxy-3-phenylpropionate and 143 mg of sodium chloride in a mixture of 2 cm³ of anhydrous tetrahydrofuran and 10 cm³ of anhydrous acetonitrile was brought to reflux for 1 hour. After cooling to a temperature in the region of 20° C., the reaction mixture was filtered through sintered glass, the solid residue was rinsed with 10 cm³ of ethyl acetate and the filtrate was concentrated under reduced pressure (2.7 kPa) at a temperature in the region of 30° C. 90 mg of an ivory-coloured foam were thereby obtained, which product was purified by preparative thin-layer chromatography on silica [Merck Silica gel 60F254 preparative plates; 20×20 cm; thickness 0.5 mm; application in solution in dichloromethane], eluting with a methanol/dichloromethane (5:95 by volume) mixture. After elution of the zone corresponding to the desired product with a methanol/dichloromethane (25:75 by volume) mixture, filtration through sintered glass and then evaporation of the solvents under reduced pressure (2.7 kPa) at a temperature in the region of 30° C., 65 mg of 4α,10β-diacetoxy-2α-benzoyloxy and 5β,20-epoxy-1β-hydroxy-9-oxo-19-nor-7,11-taxadien-13α-yl(2R,3S)-3-tert-butoxycarbonylamino-2-hydroxy-3-phenylpropionate were obtained in the form of a white foam, the characteristics of which were as follows:

¹H NMR spectrum (600 MHz; CDCl₃ at a temperature of 333° K, δ in ppm; coupling constants J in Hz): 1.15 (s, 3H: CH₃); 1.38 (s, 3H: CH₃); 1.42 (s, 9H: C(CH₃)₃); 1.72 (s, 3H: CH₃); 1.95 (s, 1H: OH); 2.00 and from 2.40 to 2.60 (respectively dd and mt, J=15 and 3, 1H each: CH₂ at position 14); 2.23 (s, 3H: COCH₃); 2.27 (s, 3H; COCH₃); 2.52 (limiting AB, J$_{ab}$=17, 1H each: CH₂ at position 6); 3.47 (d, J=7.5 Hz, 1H: H at position 3); 4.20 and 4.30 (2d, J=8, 1H each: CH₂ at position 20); 4.25 (broad s, 1H: OH at position 2'); 4.64 (mt, 1H: H at position 2'); 4.90 (broad s, 1H: H at position 5); 5.37 (broad d, J=10, 1H: H at position 3'); 5.58 (d, J=7.5, 1H: H at position 2); 5.67 (d, J=10, 1H: CONH); 6.00 (dd, J=6 and 3, 1H: H at position 13); 6.21 (mt, 1H: H at position 7); 6.35 (s, 1H: H at position 10); 7.30 (t, J=7.5, 1H: para-H of the aromatic ring at position 3'); 7.38 (t, J=7.5, 2H: meta-H of the aromatic ring at position 3'); 7.47 (d, J=7.5, 2H: ortho-H of the aromatic ring at position 3'); 7.48 (t, J=7.5, 2H: OCOC₆H₅ meta-H); 7.60 (t, J=7.5, 1H: OCOC₆H₅ para-H); 8.12 (d, J=7.5, 2H: OCOC₆H₅ ortho-H).

4α,10β-Diacetoxy-2α-benzoyloxy-5β,20-epoxy-1β,19-dihydroxy-9-oxo-7β-trifluoromethanesulphonyloxy-11-taxen-13α-yl(2R,3S)-3-tert-butoxycarbonylamino-2-hydroxy-3-phenylpropionate was prepared in the following manner:

A solution of 147 mg of 4α,10β-diacetoxy-2α-benzoyloxy-5β,20-epoxy-1β,19-dihyroxy-9-oxo-7β- trifluoromethanesulphonyloxy-11-taxen-13α-yl(2R,4S,5R)-3-tert-butoxycarbonyl-2-(4-methoxyphenol)-4-phenyl-1,3-oxazolidine-5-carboxylate in 10 cm³ of 0.1 N ethanolic hydrogen chloride solution was kept stirring at a temperature in the region of 20° C. for 5 hours under an argon atmosphere. The reaction mixture was then diluted with 50 cm³ of ethyl acetate, 10 cm³ of saturated aqueous sodium hydrogen carbonate solution and 5 cm³ of distilled water. After settling took place, the organic phase was separated and washed with 3 times 15 cm³ of distilled water, dried over magnesium sulphate, filtered through sintered glass and then concentrated to dryness under reduced pressure (2.7 kPa) at a temperature in the region of 40° C. The residue obtained was purified by preparative thin-layer chromatography on silica [4 Merck Silica gel 60F254 preparative plates; thickness 0.5 mm; application in solution in dichloromethane], eluting with a methanol/dichloromethane (5:95 by volume) mixture. After elution of the zone corresponding to the major product with a methanol/dichloromethane (25:75 by volume) mixture, filtration through sintered glass and then evaporation of the solvents under reduced pressure (0.27 kPa) at a temperature in the region of 40° C., 120 mg of 4α,10β-diacetoxy-2α-benzoyloxy-5β,20-epoxy-1β,19-dihydroxy-9-oxo-7β-trifluoromethanesulphonyloxy-11-taxen-13α-yl(2R,3S)-3-tert-butoxycarbonylamino-2-hydroxy-3-phenylpropionate were obtained in the form of a white foam, the characteristics of which were as follows:

¹H NMR spectrum (300 MHz; CDCl₃; at a temperature of 333 K, δ in ppm; coupling constants J in Hz): 1.24 (s, 3H: CH₃); 1.37 (s, 3H: CH₃); 1.37 (s, 9H: C(CH₃)₃); 1.87 (s, 1H: OH at position 1); from 2.00 to 2.25 (mt, 2H: CH₂ at position 14); 2.03 (s, 3H: CH₃); from 2.10 to 2.40 and 2.85 (2 mt, 1H each: CH₂ at position 6); 2.25 (s, 3H: COCH₃); 2.45 (s, 3H: COCH₃); 2.45 (t, J=6.5, 1H: OH at position 19); 3.37 (d, J=6, 1H: OH at position 2'); 3.95 (d, J=7, 1H: H at position 3); 4.40 (limiting AB, J=9, 2H: CH₂ at position 20); 4.65 (mt, 1H: H at position 2'); 4.75 and 4.90 (2 dd, J=13 and 6.5, 1H each: CH₂ at position 19); 4.97 (broad d, J=10, 1H: H at position 5); 5.27 (broad d, J=10, 1H: H at position 3'); 5.39 (d, J=10, 1H: CONH); 5.48 (dd, J=10 at position 8, 1H: H at position 7); 6.19 (broad t, J=9, 1H: H at position 13); 6.65 (d, J=7, 1H: H at position 2); 6.66 (s, 1H: H at position 10); from 7.30 to 7.45 (mt, 5H: aromatic H at position 3'); 7.52 (t, J=7.5, 2H: OCOC₆H₅ meta-H); 7.65 (t, J=7.5, 1H: OCOC₆H₅ para-H); 8.15 (d, J=7.5, 2H: OCOC₆H₅ ortho-H).

15 mg of 4-(N,N'-dimethylamino)pyridine and then 0.07 cm³ of acetic anhydride were added successively to a solution, maintained under an argon atmosphere at a temperature in the region of 20° C., of 280 mg of 4α-acetoxy-2α-benzoyloxy-5β,20-epoxy-1β,10β,19-trihydroxy-9-oxo-7β-trifluoromethanesulphonyloxy-11-taxen-13α-yl(2R,4S,5R)-3-tert-butoxycarbonyl-2-(4-methoxyphenyl)-4-phenyl-1,3-oxazolidine-5-carboxylate in 5 cm³ of anhydrous pyridine. After 2 hours at a temperature in the region of 20° C., 0.07 cm³ of acetic anhydride was added. Two hours later, a further 0.07 cm³ of acetic anhydride was added. After 2.5 hours at a temperature in the region of 20° C., the reaction medium was diluted with 25 cm³ of ethyl acetate and 5 cm³ of distilled water. After settling has taken place, the organic phase was separated and washed with 3 times 5 cm³ of distilled water, dried over magnesium sulphate, filtered through sintered glass and then concentrated to dryness under reduced pressure (2.7 kPa) at a temperature in the region of 40° C. 287 mg of an ivory-coloured foam are thereby obtained, which product was purified by preparative thin-layer chromatography on silica [4 Merck Silica gel 60F254 preparative plates; thickness 0.5 mm; application in solution in dichloromethane], eluting with a methanol/dichloromethane (5:95 by volume) mixture. After elution of the zone corresponding to the major product with a methanol/dichloromethane (25:75 by volume) mixture, filtration through sintered glass and then evaporation of the solvents under reduced pressure (0.27 kPa) at a temperature in the region of 40° C., 147 mg of 4α,10β-diacetoxy-2α-benzoyloxy-5β,20-epoxy-1β,19-dihydroxy-9-oxo-7β-trifluoromethanesulphonyloxy-11-taxen-13α-yl(2R,4S,5R)-3-tert-butoxycarbonyl-2-(4-methoxyphenyl)-4-phenyl-1,3-oxazolidine-5-carboxylate were obtained in the form of a white foam, the characteristics of which were as follows:

¹H NMR spectrum (400 MHz; CDCl₃; at a temperature of 333 K, δ in ppm; coupling constants J in Hz): 1.07 (s, 9H: C(CH₃)₃); 1.20 (s, 3H: CH₃); 1.34 (s, 3H: CH₃); 1.67 (s, 3H: CH₃); 1.82 (s, 1H: OH at position 1); 1.91 (unres. comp., 3H: COCH₃); 2.02 and 2.06 (2 dd, J=15 and 8.5, 1H each: CH₂ at position 14); 2.24 and 2.82 (2 mt, 1H each: CH₂ at position 6); 2.24 (s, 3H: COCH₃); 2.40 (t, J=7, 1H: OH at position 19); 3.84 (S, 3H: ArOCH₃); 3.85 (d, J=7, 1H: H at position 3); 4.30 and 4.37 (2 d, J=8, 1H each: CH₂ at position 20); 4.58 (d, J=5, 1H: H at position 2'); 4.71 and 4.83 (2 dd, J=13 and 7, 1H each: CH₂ at position 19); 4.90 (broad d, J=10, 1H: H at position 5); 5.45 (dd, J=10.5 and 7, 1H: H at position 7); 5.45 (unres. comp., 1H: H at position 3'); 6.07 (broad t, J=9, 1H: H at position 13); 6.40 (unres. comp. 1H: H at position 5'); 6.54 (s, 1H: H at position 10); 6.61 (d, J=7, 1H: H at position 2); 6.94 (d, J=8, 2H: aromatic H at the ortho positions with respect to the OCH₃); from 7.30 to 7.45 (mt, 7H: aromatic H at position 3' and aromatic H at the meta positions with respect to the OCH₃); 7.51 (t, J=7.5, 2H: OCOC₆H₅ meta-H); 7.63 (t, J=7.5, 1H: OCOC₆H₅ para-H); 8.07 (d, J=7.5, 2H: OCOC₆H₆ ortho-H).

1.26 cm³ of trifluoromethanesulphonic anhydride were added dropwise to a suspension, maintained under an argon atmosphere at a temperature in the region of −35° C., of 3.3 g of 4α-acetoxy-2-benzoyloxy-5β,20-epoxy-1β,7β,10β,19-tetrahydroxy-9-oxo-11-taxen-13α-yl(2R,4S,5R)-3-tert-butoxycarbonyl-2-(4-methoxyphenyl)-4-phenyl-1,3-oxazolidine-5-carboxylate and 1.5 g of activated 4 Å molecular sieves in 60 cm³ of anhydrous dichloromethane and 0.97 cm³ of anhydrous pyridine. After one hour at a temperature in the region of 0° C., the reaction mixture was cooled to a temperature in the region of −10° C., diluted with 20 cm³ of distilled water and filtered through sintered glass lined with Celite. After rinsing the sintered glass with 20 cm³ of dichloromethane and when settling of the filtrate has taken place, the organic phase was washed with 2 times 25 cm³ of distilled water, dried over magnesium sulphate, filtered through sintered glass and then concentrated to dryness under reduced pressure (2.7 kPa) at a temperature in the region of 40° C. 3.2 g of a yellow foam were thereby obtained, which product was purified by chromatography at atmospheric pressure on silica (0.043–0.060 mm) contained in a column 2.5 cm in diameter and 30 cm in height, eluting with 1 liter of dichloromethane and then with a methanol/dichloromethane (1:99 by volume) mixture, collecting 15-cm³ fractions. The fractions containing only the desired product were pooled and concentrated to dryness under reduced pressure (2.7 kPa) at 40° C. for 2 hours. 1.35 g of 4α-acetoxy-2α-benzoyloxy-5β,20-epoxy-1β,10β,19-trihydroxy-9-oxo-7β-trifluoromethane sulphonyloxy-11-taxen-13α-yl(2R,4S,5R)-3-tert-butoxycarbonyl-2-(4-methoxyphenyl)-4-phenyl-1,3-oxazolidine-5-carboxylate were thereby obtained in the form of a white foam, the characteristics of which were as follows:

¹H NMR spectrum (300 MHz; CDCl₃; at a temperature of 333 K, δ in ppm; coupling constants J in Hz): 1.08 (s, 9H:

C(CH$_3$)$_3$); 1.23 (s, 6H: CH$_3$); 1.56 (s, 3H: CH$_3$); 1.78 (s, 1H: OH at position 1); 1.93 (unres. comp., 3H: COCH$_3$); from 1.85 to 2.15 and 2.76 (2 mts, 1H each: CH$_2$ at position 6); from 1.85 to 2.15 and 2.20 (respectively mt and dd, J=16 and 9 Hz, 1H each: CH$_2$ at position 14); 2.48 (t, J=6 Hz, 1H: OH at position 19); 3.82 (s, 3H: ArOCH$_3$); 3.90 (d, J=7, 1H: H at position 3); 3.96 (broad s, 1H: OH at position 10); 4.30 and 4.45 (2 d, J=9, 1H each: CH$_2$ at position 20); 4.58 (d, J=5, 1H: H at position 2'); 4.75 and 4.86 (2 dd, J=13 and 6, 1H each: CH$_2$ at position 19); 4.91 (broad d, J=10, 1H: H at position 5); 5.30 (broad s, 1H: H at position 10); 5.40 (d, J=11 and 8, 1H: H at position 7); 5.45 (unres. comp., 1H: H at position 3'); 6.15 (broad t, J=9, 1H: H at position 13); 6.40 (unres. comp., 1H: H at position 5'); 6.58 (d, J=7, 1H: H at position 2); 6.95 (d, J=8.2H: aromatic H at the ortho positions with respect to the OCH$_3$); from 7.25 to 7.45 (mt, 7H: aromatic H at position 3' and aromatic H at the meta positions with respect to the OCH$_3$); 7.50 (t, J=7.5, 2H: OCOC$_6$H$_5$ meta-H); 7.66 (t, J=7.5, 1H: OCOC$_6$H$_5$ para-H); 8.06 (d, J=7.5, 2H: OCOC$_6$H$_5$ ortho-H).

1.03 cm$^3$ of acetic acid were added dropwise to a suspension, maintained under an argon atmosphere at a temperature in the region of 20° C., of 4.4 g of 4α-acetoxy-2α-benzoyloxy-5β,20-epoxy-1β-hydroxy-9-oxo-7β,10β,19-tris(2,2,2-trichloroethoxycarbonyloxy)-11-taxen-13α-yl (2R,4S,5R)-3-tert-butoxycarbonyl-2-(4-methoxyphenyl)-4-phenyl-1,3-oxazolidine-5-carboxylate and 4.88 g of zinc powder in 40 cm$^3$ of ethyl acetate. After 2 hours at a temperature in the region of 20° C., the reaction mixture was brought to a temperature in the region of 40° C., and 4.88 g of zinc powder and 1.03 cm$^3$ of acetic acid were added. After 1 hour at a temperature in the region of 40° C., the reaction mixture was cooled to a temperature in the region of 20° C., diluted with 200 cm$^3$ of ethyl acetate and 100 cm$^3$ of saturated aqueous sodium hydrogen carbonate solution and filtered through sintered glass lined with Celite. After rinsing the sintered glass with 75 cm$^3$ of ethyl acetate, and when settling of the filtrate has took place, the organic phase was washed with 4 times 100 cm$^3$ of distilled water, dried over magnesium sulphate, filtered through sintered glass and then concentrated to dryness under reduced pressure (2.7 kPa) at a temperature in the region of 40° C. 3.3 g of 4α-acetoxy-2α-benzoyloxy-5β,20-epoxy-1β,7β,10β,19-tetrahydroxy-9-oxo-11-taxen-13α-yl(2R,4S,5R)-3-tert-butoxycarbonyl-2-(4-methoxyphenyl)-4-phenyl-1,3-oxazolidine-5-carboxylate were thereby obtained in the form of a white foam, the characteristics of which were as follows:

$^1$H NMR spectrum (300 MHz; CDCl$_3$; at a temperature of 333 K, δ in ppm; coupling constants J in Hz): 1.07 (s, 9H: C(CH$_3$)$_3$); 1.22 (s, 3H: CH$_3$); 1.24 (s, 3H: CH$_3$); 1.52 (s, 3H: CH$_3$); 1.67 (s, 1H: OH at position 1); 1.85 (unres. comp., 3H: COCH$_3$); from 1.85 to 2.10 and 2.68 (2 mt, 1H each: CH$_2$ position 6); from 1.85 to 2.10 and 2.14 (respectively mt and dd, J=16 and 9, 1H each: CH$_2$ at position 14); 2.68 (d, J=10, 1H: OH at position 7); 3.21 (dd, J=8 and 5, 1H: OH at position 19); 3.80 (d, J=7, 1H; H at position 3); 3.83 (s, 3H: ArOCH$_3$); 4.02 (broad s, 1H: OH at position 10); 4.02 and 4.30 (2 d, J=9, 1H each: CH$_2$ at position 20); 4.28 (mt, 1H: H at position 7); 4.57 (d, J=5, 1H: H at position 2'); 4.71 and 4.80 (2 dd respectively J=13 and 5 and J=13 and 8, 1H each: CH$_2$ at position 19); 4.94 (broad d, J=10, 1H: H at position 5); 5.20 (broad s, 1H: H at position 10); 5.42 (unres. comp., 1H: H at position 3'); 5.80 (d, J=7, 1H: H at position 2); 6.14 (broad t, J=9, 1H: H at position 13); 6.39 (unres. comp., 1H: H at position 5'); 6.94 (d, J=8, 2H: aromatic H at the ortho positions with respect to the OCH$_3$); from 7.25 to 7.45 (mt, 7H: aromatic H at position 3' and aromatic H at the meta positions with respect to the OCH$_3$); 7.50 (t, J=7.5, 2H: OCOC$_6$H$_5$ meta-H); 7.63 (t, J=7.5, 1H: OCOC$_6$H$_5$ para-H); 8.03 (d, J=7.5, 2H: OCOC$_6$H$_5$ ortho-H).

3.3 g of dicyclohexylcarbodiimide and then 0.366 g of 4-(N,N-dimethylamino)pyridine were added successively to a solution, maintained under an argon atmosphere at a temperature in the region of 20° C., of 10.86 g of 4α-acetoxy-2α-benzoyloxy-5β,20-epoxy-1β-hydroxy-9-oxo-7β,10β,19-tris(2,2,2-trichloroethoxycarbonyloxy)-11-taxene and 5.19 g of (2R,4S,5R)-(2R,4S,5R)-3-tert-butoxycarbonyl-2-(4-methoxyphenyl)-4-phenyl-1,3-oxazolidine-5-carboxylic acid in 150 cm$^3$ of ethyl acetate. After 16 hours at a temperature in the region of 20° C., the suspension obtained was sintered through sintered glass. After rinsing the sintered glass with 50 cm$^3$ of ethyl acetate, the filtrate was diluted with 100 cm$^3$ of ethyl acetate, washed with 100 cm$^3$ of saturated aqueous sodium hydrogen carbonate solution and then with 4×100 cm$^3$ of distilled water, dried over magnesium sulphate, filtered through sintered glass and then concentrated to dryness under reduced pressure (2.7 kPa) at a temperature in the region of 40° C. 15.7 g of 4α-acetoxy-2α-benzoyloxy-5β,20-epoxy-1β-hydroxy-9-oxo-7β,10β,19-tris(2,2,2-trichloroethoxycarbonyloxy)-11-taxen-13α-yl(2R,4S,5R)-3-tert-butoxycarbonyl-2-(4-methoxyphenyl)-4-phenyl-1,3-oxazolidine-5-carboxylate were thereby obtained in the form of a white foam, the characteristics of which were as follows:

$^1$H NMR spectrum (400 MHz; CDCl$_3$; at a temperature of 333 K, δ in ppm; coupling constants J in Hz): 1.06 (s, 9H: C(CH$_3$)$_3$); 1.27 (s, 3H: CH$_3$); 1.33 (s, 3H: CH$_3$); 1.68 (s, 3H: CH$_3$); 1.86 and 2.65 (2 mt, 1H each: CH$_2$ at position 6); 1.92 (s, 3H: COCH$_3$); 2.07 and 2.26 (2 dd, J=15.5 and 9, 1H each: CH$_2$ at position 14); 3.84 (s, 3H: ArOCH$_3$); 3.94 (d, J=7, 1H: H at position 3); 4.17 and 4.34 (2 d, J=9, 1H each: CH$_2$ at position 20); 4.58 (d, J=5, 1H: H at position 2'); 4.61 and 4.93 (2 d, J=12, 1H each: COOCH$_2$CCl$_3$); 4.75 and 4.81 (2 d, J=12, 1H each: COOCH$_2$CCl$_3$); 4.75 and 4.99 (2 d, J=12, 1H each: COOCH$_2$CCl$_3$); 4.92 (broad d, J=10, 1H: H at position 5); 5.43 (d, J=5, 1H: H at position 3'); 5.43 (limiting AB, J=10.5, 2H: CH$_2$ at position 19); 5.58 (dd, J=10.5 and 7, 1H: H at position 7); 6.13 (broad t, J=9, 1H: H at position 13); 6.20 (s, 1H: H at position 10); 6.38 (s, 1H: H at position 5'); 6.39 (d, J=7, 1H: H at position 2); 6.94 (d, J=8, 2H: aromatic H at the ortho positions with respect to the OCH$_3$); from 7.25 to 7.45 (mt, 7H: aromatic H at position 3' and aromatic H at the meta positions with respect to the OCH$_3$); 7.50 (t, J=7.5, 2H: OCOC$_6$H$_5$ meta-H); 7.62 (t, J=7.5, 1H: OCOC$_6$H$_5$ para-H); 8.04 (d, J=7.5, 2H: OCOC$_6$H$_5$ ortho-H).

EXAMPLE 2

A suspension, maintained under an argon atmosphere, of 187.3 mg of 4α-acetoxy-2α-benzoyloxy-5β,20-epoxy-1β,10β,19-trihydroxy-9-oxo-7β-trifluoromethylsulphonyloxy-11-taxen-13α-yl(4S,5R)-3-tert-butoxycarbonyl-2,2-dimethyl-4-phenyl-5-oxazolidinecarboxylate, 112 mg of activated 4 Å molecular sieves and 171 mg of sodium chloride in a mixture of 1.7 cm$^3$ of anhydrous tetrahydrofuran and 6.8 cm$^3$ of anhydrous acetonitrile was brought to reflux for 1.5 hours. After cooling to a temperature in the region of 20° C., the reaction mixture was filtered through sintered glass, the solid residue was rinsed with 10 cm$^3$ of acetonitrile and the filtrate was concentrated under reduced pressure (2.7 kPa) at a temperature in the region of 40° C. The residue obtained was purified by preparative thin-layer chromatography on silica (4 Merck Silica gel 60F254 preparative plates; 20×20 cm; thickness 0.5 mm; application in solution in dichloromethane], eluting with a methanol/ dichloromethane (3:97 by volume) mixture. After elution of the zone corresponding to the desired product with a methanol/dichloromethane (15:85 by volume) mixture, filtration through sintered glass and then evaporation of the solvents under reduced pressure (2.7 kPa) at a temperature in the region of 40° C., 55 mg of 4α-acetoxy-2α-benzoyloxy-5α,20-epoxy-1α,10α-dihydroxy-9-oxo-19-nor-7,11-taxadien-13α-yl(4S,5R)-3-tert-butoxycarbonyl-2,2-dimethyl-4-phenyl-5-oxazolidinecarboxylate were obtained in the form of a white foam, the characteristics of which were as follows:

$^1$H NMR spectrum (400 MHz; CDCl$_3$; δ in ppm; coupling constants J in Hz): 1.13 (unres. comp., 9H: C(CH$_3$)$_3$); 1.20 (s, 3H: CH$_3$); 1.31 (s, 3H: CH$_3$); 1.70 (s, 3H:CH$_3$); 1.73 (s, 3H: CH$_3$); 1.83 (s, 6H: CH$_3$ and COCH$_3$); 1.90 and 2.43 (2 dd, respectively J=16 and 6 and J=16 and 10, 1H each: CH$_2$ at position 14); 1.95 (s, 1H: OH at position 1); 2.45 and 2.60 (2 broad d, J=18, 1H each: CH$_2$ at position 6); 3.40 (broad d, J=8, 1H: H at position 3); 3.78 (unres. comp., 1H: OH at position 10); 4.10 and 4.26 (2 d, J=8, 2H: CH$_2$ at position 20); 4.56 (d, J=6, 1H: H at position 2'); 4.88 (broad s, 1H: H at position 5); 5.19 (unres. comp., 1H: H at position 3'); 5.19 (s, 1H: H at position 10); 5.50 (d, J=8, 1H: H at position 2); 6.03 (dd, J=10 and 6, 1H: H at position 13); 6.27 (mt, 1H: H at position 7); 7.35 (mt, 5H: aromatic H at position 3'); 7.48 (t, J=7.5, 2H: OCOC$_6$H$_5$ meta-H); 7.62 (t, J=7.5, 1H: OCOC$_6$H$_5$ para-H); 8.08 (d, J=7.5, 2H: OCOC$_6$H$_5$ ortho-H).

4α-Acetoxy-2α-benzoyloxy-5β,20-epoxy-1β,10β-dihydroxy-9-oxo-19-nor-7,11-taxadien-13α-yl(4S,5R)-3-tert-butoxycarbonyl-2,2-dimethyl-4-phenyl-5-oxazolidinecarboxylate treated with formic acid at 20° C. yielded 4α-acetoxy-2α-benzoyloxy-5β,20-epoxy-1β,10β-dihydroxy-9-oxo-19-nor-7,11-taxadien-13α-yl(2R,3S)-3-amino-2-hydroxy-3-phenylpropionate, which reacted with di-tert-butyl dicarbonate in the presence of sodium hydrogen carbonate in dichloromethane at 20° C. yields 4α-acetoxy-2α-benzoyloxy-5β,20-epoxy-1β,10β-dihydroxy-9-oxo-19-nor-7,11-taxadien-13α-yl(2R,3S)-3-tert-butoxycarbonylamino-2-hydroxy-3-phenylpropionate.

4α-Acetoxy-2α-benzoyloxy-5β,20 -epoxy-1β,10β,19-trihydroxy-9-oxo-7β-trifluoromethyl-sulphonyloxy-11-taxen-13α-yl(4S,5R)-3-tert-butoxycarbonyl-2,2-dimethyl-4-phenyl-5-oxazolidinecarboxylate was prepared in the following manner:

0.155 cm$^3$ of trifluoromethanesulphonic anhydride was added dropwise to a suspension, maintained under an argon atmosphere at a temperature in the region of −35° C., of 316 mg of 4α-acetoxy-2α-benzoyloxy-5β,20-epoxy-1β,7β,10β,19-tetrahydroxy-9-oxo-11-taxen-13α-yl(4S,5R)-3-tert-butoxycarbonyl-2,2-dimethyl-4-phenyl-5-oxazolidinecarboxylate and 25 mg of activated 4 Å molecular sieves in 3 cm$^3$ of anhydrous dichloromethane and 0.12 cm$^3$ of anhydrous pyridine. After 50 minutes at a temperature in the region of 0° C., the reaction mixture was cooled to a temperature in the region of −15° C. and diluted with 5 cm$^3$ of distilled water, 3 cm$^3$ of saturated aqueous sodium chloride solution and 10 cm$^3$ of dichloromethane. After settling has taken place, the aqueous phase was separated and extracted with 5 cm$^3$ of dichloromethane. The combined organic phases were washed with 5 cm$^3$ of distilled water, dried over magnesium sulphate, filtered through sintered glass and then concentrated to dryness under reduced pressure (2.7 kPa) at a temperature in the region of 40° C. 373.6 mg of a crude product were thereby obtained, which product was purified by preparative thin-layer chromatography on silica [10 Merck Silica gel 60F254 preparative plates; 20×20 cm; thickness 1 mm, application in solution in dichloromethane], eluting with a methanol/dichloromethane (5:95 by volume) mixture. After elution of the zone corresponding to the desired product with a methanol/dichloromethane (15:85 by volume) mixture, filtration through sintered glass and then evaporation of the solvents under reduced pressure (2.7 kPa) at a temperature in the region of 40° C., 187.3 mg of 4α-acetoxy-2α-benzoyloxy-5⊕,20-epoxy-1β,10β,19-trihydroxy-9-oxo-7β-trifluoromethyl-sulphonyloxy-11-taxen-13α-yl(4S,5R)-3-tert-butoxycarbonyl-2,2-dimethyl-4-phenyl-5-oxazolidinecarboxylate, were obtained in the form of a white foam, the characteristics of which were as follows:

$^1$H NMR spectrum (400 MHz; CDCl$_3$; at a temperature of 333 K; δ in ppm; coupling constants J in Hz): 1.23 (s, 9H: (CH$_3$)$_3$); 1.29, (s, 6H: CH$_3$); 1.75 (s, 1H: OH at position 1); 1.79 (s, 3H: CH$_3$); 1.85 (s, 3H: CH$_3$); 2.01 (s, 3H: COCH$_3$; 2.03 (s, 3H: CH$_3$); 2.12 and 2.23 (2 dd, J=16 and 9, 1H each: CH$_2$ at position 14); 2.13 and 2.81 (2 mts, 1H each: CH$_2$ at position 6); 2.39 (t, J=7, 1H: OH at position 19); 3.91 (broad s, 1H: OH at position 10); 4.03 (d, J=7, 1H: H at position 3); 4.37 (limiting AB, J=9 2H: CH$_2$ at position 20); 4.47 (d, J=7, 1H: H at position 2'); 4.78 and 4.89 (2 dd, J=12 and 7, 1H each: CH$_2$ at position 19); 4.94 (broad d, J=10, 1H: H at position 5); 5.17 (d, J=7, 1H: H at position 3'); 5.43 (broad s, 1H: H at position 10); 5.50 (dd, J=11 and 8, 1H: H at position 7); 6.30 (broad t, J=9, 1H: H at position 13); 6.58 (d, J=7, 1H: H at position 2); 7.38 (mt, 5H: aromatic H at position 3'); 7.50 (t, J=7.5, 2H: OCOC$_6$H$_5$ meta-H); 7.63 (t, J=7.5, 1H: OCOC$_6$H$_5$ para-H); 8.07 (d, J=7.5, 2H: OCOC$_6$H$_5$ ortho-H).

4α-Acetoxy-2α-benzoyloxy-5β,20-epoxy-1β,7β,10β,19-tetrahydroxy-9-oxo-11-taxen-13α-yl-(4S,5R)-3-tert-butoxycarbonyl-2,2-dimethyl-4-phenyl-5-oxazolidinecarboxylate was prepared in the following manner:

0.117 cm$^3$ of acetic acid was added dropwise to a suspension, maintained under an argon atmosphere at a temperature in the region of 20° C., of 500 mg of 4α-acetoxy-2α-benzoyloxy-5β,20-epoxy-1β-hydroxy-9-oxo-7β,10β,19-tris(2,2,2-trichloroethoxycarbonyloxy)-11-taxen-13α-yl(4S,5R)-3-tert-butoxycarbonyl-2,2-dimethyl-4-phenyl-5-oxazolidinecarboxylate and 585 mg of zinc powder in 1.5 cm$^3$ of ethyl acetate. After 20 minutes at a temperature in the region of 20° C., the reaction mixture was diluted with 15 cm$^3$ of ethyl acetate, 10 cm$^3$ of saturated aqueous sodium hydrogen carbonate solution and 5 cm$^3$ of distilled water and filtered through sintered glass lined with Celite. After rinsing the sintered glass with 5 cm$^3$ of ethyl acetate, and when settling of the filtrate took place, the aqueous phase was separated and extracted with 5 cm$^3$ of ethyl acetate. The combined organic phases were washed with 5 cm$^3$ of distilled water, dried over magnesium sulphate, filtered through sintered glass and then concentrated to dryness under reduced pressure (2.7 kPa) at a temperature in the region of 40° C. 316 mg of 4α-acetoxy-2α-benzoyloxy-5β,20-epoxy-1β,7β,10β,19-tetrahydroxy-9-oxo-11-taxen-13α-yl(4S,5R)-3-tert-butoxycarbonyl-2,2-dimethyl-4-phenyl-5-oxazolidinecarboxylate were thereby obtained in the form of a white foam, the characteristics of which was as follows:

$^1$H NMR spectrum (400 MHz; CDCl$_3$; δ in ppm; coupling constants J in Hz): 1.10 (unres. comp., 9H: C(CH$_3$)$_3$); 1.24 (s, 3H: CH$_3$); 1.27 (s, 3H: CH$_3$); 1.67 (unres. comp., 1H: OH at position 1); 1.77 (s, 3H: CH$_3$); 1.82 (s, 3H: CH$_3$); 1.88 (s, 3H: CH$_3$); 2.01 (s, 3H: COCH$_3$); 2.05 and 2.70 (2 mt, 1H each: CH$_2$ at position 6); 2.12 (limiting AB J=15 and 9, 2H: CH$_2$ at position 14); 3.20 (unres. comp., 1H: OH); 3.96 (d, J=7, 1H: H at position 3); 4.07 and 4.32 (2 d, J=8.5, 1H each: CH$_2$ at position 20); 4.07 (unres. comp., 1H: OH); 4.39 (mt, 1H: H at position 7); 4.46 (d, J=7, 1H: H at position 2'); 4.74 and 4.81) respectively broad d and dd, J=11 and J=11 and 4, 1H each: CH$_2$ at position 19): 4.98 (broad d, J=10, 1H: H at position 5); 5.08 (unres. comp., 1H: H at position 3'); 5.28 (s, 1H: H at position 10); 5.82 (d, J=7), 1H: H at position 2); 6.27 (broad t, J=9, 1H: H at position 13); 7.35 (mt, 5H: aromatic H at position 3'); 7.50 (t, J=7.5, 2H: OCOC$_6$H$_5$ meta-H); 7.63 (t, J=7.5, 1H: OCOC$_6$H$_5$ para-H); 8.04 (d, J=7.5, 2H: OCOC$_6$H$_5$ ortho-H).

4α-Acetoxy-2α-benzoyloxy-5β,20-epoxy-1β-hydroxy-9-oxo-7β,10β,19-tri-((2,2,2-trichloroethoxycarbonyloxy)-11-taxen-13α-yl(4S,5R)-3-tert-butoxycarbonyl-2,2-dimethyl-4-phenyl-5-oxazolidinecarboxylate was prepared in the following manner:

3.31 g of dicyclohexylcarbodiimide and then 0.370 g of 4-(N,N-dimethylamino)pyridine were added successively to a solution, maintained under an argon atmosphere at a temperature in the region of 20° C., of 10.9 g of 4α-acetoxy-2-benzoyloxy-5β,20-epoxy-1β-hydroxy-9-oxo-7β,10β,19-tris(2,2,2-trichloroethoxycarbonyloxy)-11-taxene and 4.19 g of (4S,5R)-3-tert-butoxycarbonyl-2,2-dimethyl-4-phenyl-5-oxazolidinecarboxylic acid in 50 cm$^3$ of anhydrous toluene. After 20 hours at a temperature in the region of 20° C., the crude reaction mixture is purified directly by application to a chromatography column at atmospheric pressure containing 400 g of silica (0.063–0.2 mm) contained in a column 5 cm in diameter, eluting with a methanol/dichloromethane (0.5:99.5, then 1:99 by volume) mixture, collecting 50-cm$^3$ fractions. Fractions containing only the desired product were pooled and concentrated to dryness under reduced pressure (2.7 kPa) at 40° C. for 2 hours. 11.0 g of 4α-acetoxy-2α-benzoyloxy-5β,20-epoxy-1β-hydroxy-9-oxo-7β,10β,19-tris (2,2,2-trichloroethoxycarbonyloxy)-11-taxen-13α-yl(4S, 5R)-3-tert-butoxycarbonyl-2,2-dimethyl-4-phenyl-5-oxazolidinecarboxylate were thereby obtained in the form of a white foam, the characteristics of which were as follows:

$^1$H NMR spectrum (400 MHz; CDCl$_3$; at a temperature of 333 K; δ in ppm; coupling constants J in Hz): 1.22 (unres. comp., 9H: C(CH$_3$)$_3$); 1.31 (s, 3H: CH$_3$); 1.37 (s, 3H: CH$_3$); 1.77 (s, 3H: CH$_3$); 1.85 (s, 3H: CH$_3$); 1.85 and 2.69 (2 mt, 1H each: CH$_2$ at position 6); 2.01 (s, 3H: CH$_3$); 2.09 (s, 3H: COCH$_3$); 2.14 and 2.25 (2 dd, J=15 and 9, 1H each: CH$_2$ at position 14); 4.03 (d, J=7, 1H: H at position 3); 4.20 and 4.37 (2 d, J=8.5, 1H each: CH$_2$ at position 20); 4.49 (d, J=7, 1H: H at position 2'); 4.64 and 4.94 (2 d, J=12, 1H each: COOCH$_2$CCl$_3$); 4.78 and 4.82 (2 d, J=12, 1H each: COOH$_2$CCl$_3$); 4.78 and 4.97 (2 d, J=12, 1H each: COOCH$_2$CCl$_3$); 4.96 (broad d, J=10, 1H: H at position 5); 5.16 (d, J=7, 1H: H at position 3'); 5.44 and 5.49 (2 d, J=10, 2H: CH$_2$ at position 19); 5.66 (dd, J=11 and 8, 1H: H at position 7); 6.29 (broad t, J=9, 1H: H at position 13); 6.29 (s, 1H: H at position 10); 6.44 (d, J=7, 1H: H at position 2); from 7.30 to 7.45 (mt, 5H: aromatic H at position 3'); 7.50 (t, J=7.5, 2H: OCOC$_6$H$_5$ meta-H); 7.63 (t, J=7.5, 1H: OCOC$_6$H$_5$ para-H); 8.07 (d, J=7.5, 2H: OCOC$_6$H$_5$ ortho-H).

The new products of general formula (I) in which Z represents a radical of general formula (II) manifest significant inhibitory activity with respect to abnormal cell proliferation, and possess therapeutic properties permitting the treatment of patients having pathological conditions associated with abnormal cell proliferation. The pathological conditions include the abnormal cell proliferation of malignant or non-malignant cells of various tissues and/or organs, comprising, without implied limitation, muscle, bone or connective tissue, the skin, brain, lungs, sex organs, the lymphatic or renal systems, mammary or blood cells, the liver, the digestive system, pancreas and thyroid or adrenal glands. These pathological conditions can also include psoriasis, solid tumours, cancers of the ovary, breast, brain, prostate, colon, stomach, kidney or testicles, Kaposi's sarcoma, cholangiocarcinoma, choriocarcinoma, neuroblastoma, Wilms'to tumour, Hodgkin's disease, melanoma, multiple myeloma, chronic lymphocytic leukaemia and acute or chronic granulocytic lymphoma. The new products according to the invention are especially useful for the treatment of cancer of the ovary. The products according to the invention may be used to prevent or delay the appearance or reappearance of the pathological conditions, or to treat these pathological conditions.

The products according to the invention may be administered to a patient according to different dosage forms suited to the chosen administration route, which is preferably the parenteral route. Parenteral administration comprises intravenous, intraperitoneal, intramuscular or subcutaneous administration. Intraperitoneal or intravenous administration is more especially preferred.

The present invention also comprises pharmaceutical compositions containing at least one product of general formula (I), in a sufficient amount suitable for use in human or veterinary therapy. The compositions may be prepared according to the customary methods, using one or more pharmaceutically acceptable adjuvants, vehicles or excipients. Suitable vehicles include diluents, sterile aqueous media and various non-toxic solvents. Preferably, the compositions take the form of aqueous solutions or suspensions, injectable solutions which can contain emulsifying agents, colourings, preservatives or stabilizers. However, the compositions can also take the form of tablets, pills, powders or granules which can be administered orally.

The choice of adjuvants or excipients may be determined by the solubility and the chemical properties of the product, the particular mode of administration and good pharmaceutical practice.

For parenteral administration, sterile, aqueous or non-aqueous solutions or suspensions are used. For the preparation of non-aqueous solutions or suspensions, natural vegetable oils such as olive oil, sesame oil or liquid petroleum, or injectable organic esters such as ethyl oleate, may be used. The sterile aqueous solutions can consist of a solution of a pharmaceutically acceptable salt dissolved in water. The aqueous solutions are suitable for intravenous administration provided the pH is appropriately adjusted and the solution is made isotonic, for example with a sufficient amount of sodium chloride or glucose. The sterilization may be carried out by heating or by any other means which does not adversely affect the composition.

It is clearly understood that all the products participating in the compositions according to the invention must be pure and non-toxic in the amounts used.

The compositions can contain at least 0.01% of therapeutically active product. The amount of active product in a composition is such that a suitable dosage can be prescribed. Preferably, the compositions are prepared in such a way that a single dose contains from 0.01 to 1000 mg approximately of active product for parenteral administration.

The therapeutic treatment may be performed concurrently with other therapeutic treatments including antineoplastic drugs, monoclonal antibodies, immunotherapy or radiotherapy or biological response modifiers. The response modifiers include, without implied limitation, lymphokines and cytokines such as interleukins, interferons (α, β or δ)

and TNF. Other chemotherapeutic agents which are useful in the treatment of disorders due to abnormal cell proliferation include, without implied limitation, alkylating agents, for instance nitrogen mustards such as mechlorethamine, cyclophosphamide, melphalan and chlorambucil, alkyl sulphonates such as busulfan, nitrosoureas such as carmustine, lomustine, semustine and streptozocin, triazines such as dacarbazine, antimetabolites such as folic acid analogues, for instance methotrexate, pyrimidine analogues such as fluorouracil and cytarabine, purine analogues such as mercaptopurine and thioguanine, natural products, for instance vinca alkaloids such as vinblastine, vincristine and vindesine, epipodophyllotoxins such as etoposide and teniposide, antibiotics such as dactinomycin, daunorubicin, doxorubicin, bleomycin, plicamycin and mitomycin, enzymes such as L-asparaginase, various agents such as coordination complexes of platinum, for instance cisplatin, substituted ureas such as hydroxyurea, methylhydrazine derivatives such as procarbazine, adrenocortical suppressants such as mitotane and aminoglutethimide, hormones and antagonists such as adrenocorticosteroids such as prednisone, progestins such as hydroxyprogesterone caproate, methoxyprogesterone acetate and megestrol acetate, oestrogens such as diethylstilboestrol and ethynyloestradiol, antioestrogens such as tamoxifen, and androgens such as testosterone propionate and fluoxymesterone.

The doses used for carrying out the methods according to the invention are those which permit a prophylactic treatment or a maximum therapeutic response. The doses vary according to the administration form, the particular product selected and features distinctive to the subject to be treated. In general, the doses are those which are therapeutically effective for the treatment of disorders due to abnormal cell proliferation. The products according to the invention may be administered as often as necessary to obtain the desired therapeutic effect. Some patients may respond rapidly to relatively high or low doses, and then require low or zero maintenance doses. Generally, low doses will be used at the beginning of the treatment and, if necessary, increasingly stronger doses will be administered until an optimum effect is obtained. For other patients, it may be necessary to administer maintenance doses 1 to 8 times a day, and preferably 1 to 4 times, according to the physiological requirements of the patient in question. It is also possible that some patients may require the use of only one to two daily administrations.

In man, the doses are generally between 0.01 and 200 mg/kg. For intraperitoneal administration, the doses will generally be between 0.1 and 100 mg/kg, preferably between 0.5 and 50 mg/kg and still more specifically between 1 and 10 mg/kg. For intravenous administration, the doses are generally between 0.1 and 50 mg/kg, preferably between 0.1 and 5 mg/kg and still more specifically between 1 and 2 mg/kg. It is understood that, in order to choose the most suitable dosage, account should be taken of the administration route, the patient's weight, general state of health and age and all the factors which may influence the efficacy of the treatment.

The example which follows illustrates a composition according to the invention.

EXAMPLE 40 mg of the product obtained in Example 1 are dissolved in 1 cm³ of Emulphor EL 620 and 1 cm³ of ethanol, and the solution is then diluted by adding 18 cm³ of physiological saline.

The composition is administered by perfusion over 1 hour by introduction in physiological solution.

We claim:

1. A taxoid of general formula (I):

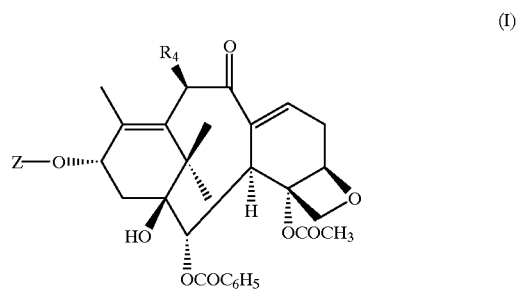

in which:

Z represents a hydrogen atom or a radical of general formula (II):

in which:

$R_1$ represents a benzoyl radical unsubstituted or substituted with one or more identical or different atoms or radicals selected from halogen atoms, alkyl radicals containing 1 to 4 carbon atoms, alkoxy radicals containing 1 to 4 carbon atoms or trifluoromethyl radicals, a thenoyl or a furoyl radical or a radical $R_2$—O—CO— in which $R_2$ represents:

an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being unsubstituted or substituted with one or more substituents selected from halogen atoms, hydroxyl radicals, alkoxy radicals containing 1 to 4 carbon atoms, dialkylamino radicals in which each alkyl portion contains 1 to 4 carbon atoms, piperidino or morpholino radicals, 1-piperazinyl radicals (unsubstituted or substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl radicals (unsubstituted or substituted with one or more atoms or radicals selected from halogen atoms, alkyl radicals containing 1 to 4 carbon atoms or alkoxy radicals containing 1 to 4 carbon atoms), cyano or carboxyl radicals or alkoxycarbonyl radicals in which the alkyl portion contains 1 to 4 carbon atoms, a phenyl or α- or β-naphthyl radical unsubstituted or substituted with one or more atoms or radicals selected from halogen atoms, alkyl radicals containing 1 to 4 carbon atoms, alkoxy radicals containing 1 to 4 carbon atoms, or a 5-membered aromatic heterocyclic radical, or a saturated heterocyclic radical containing 4 to 6 carbon atoms, unsubstituted or substituted with one or more alkyl radicals containing 1 to 4 carbon atoms;

$R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical unsubstituted or substituted with one or more atoms or radicals selected from halogen atoms, alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more identical or different hetero atoms selected from nitrogen, oxygen and sulphur atoms and unsubstituted or substituted with one or more identical or different substituents selected from halogen atoms, alkyl, aryl, amino, alkylamino, dialkylamino, alkoxycarbonylamino, acyl, arylcarbonyl, cyano, carboxyl, carbamoyl, alkylcarbamoyl, dialkylcarbamoyl or alkoxycarbonyl radicals, with the proviso that, in the substituents of the phenyl, α- or β-naphthyl and aromatic heterocyclic radicals, the alkyl radicals and the alkyl portions of the other radicals contain 1 to 4 carbon atoms, the alkenyl and alkynyl radicals contain 2 to 8 carbon atoms, and the aryl radicals are phenyl or α- or β-naphthyl radicals, $R_4$ represents a hydrogen atom, a hydroxyl radical, an alkoxy radical containing 1 to 6 carbon atoms in an unbranched or branched chain, an alkenyloxy radical containing 3 to 6 carbon atoms in an unbranched or branched chain, an alkynyloxy radical containing 3 to 6 carbon atoms in an unbranched or branched chain, a cycloalkyloxy radical containing 3 to 6 carbon atoms, a cycloalkenyloxy radical containing 3 to 6 carbon atoms, an alkanoyloxy radical in which the alkanyl portion contains 1 to 6 carbon atoms in an unbranched or branched chain, an alkenoyloxy radical in which the alkenoyl portion contains 3 to 6 carbon atoms in an unbranched or branched chain, an alkynoyloxy radical in which the alkynoyl portion contains 3 to 6 carbon atoms in an unbranched or branched chain, a cycloalkanoyloxy radical containing 1 to 6 carbon atoms, an alkoxyacetyl radical in which the alkyl portion contains 1 to 6 carbon atoms in an unbranched or branched chain, an alkylthioacetyl radical in which the alkyl portion contains 1 to 6 carbon atoms in an unbranched or branched chain or an alkyloxycarbonyloxy radical in which the alkyl portion contains 1 to 6 carbon atoms in an unbranched or branched chain, these radicals being unsubstituted or substituted with one or more halogen atoms, with an alkoxy radical containing 1 to 4 carbon atoms, an alkylthio radical containing 1 to 4 carbon atoms or a carboxyl radical, an alkyloxycarbonyl radical in which the alkyl portion contains 1 to 4 carbon atoms, a cyano or carbamoyl radical or an N-alkylcarbamoyl or N,N-dialkylcarbamoyl radical in which each alkyl portion contains 1 to 4 carbon atoms or, with the nitrogen atom to which it is linked, forms a saturated 5- or 6-membered heterocyclic radical optionally containing a second hetero atom selected from oxygen, sulphur or nitrogen atoms, unsubstituted or substituted with an alkyl radical containing 1 to 4 carbon atoms or a phenyl radical or a phenylalkyl radical in which the alkyl portion contains 1 to 4 carbon atoms, or alternatively $R_4$ represents a carbamoyloxy radical, an alkylcarbamoyloxy radical in which the alkyl portion contains 1 to 4 carbon atoms, a dialkylcarbamoyloxy radical in which each alkyl portion contains 1 to 4 carbon atoms, a benzoyloxy radical or a heterocyclic radical attached to a carbonyloxy group in which radical the heterocyclic portion represents a 5- or 6-membered aromatic heterocycle containing one or more hetero atoms selected from oxygen, sulphur and nitrogen atoms.

2. A taxoid according to claim 1 wherein Z represents a hydrogen atom or a radical of general formula (II) in which $R_1$ represents a benzoyl radical or a radical $R_2$—O—CO— in which $R_2$ represents a tert-butyl radical, and $R_3$ represents an alkyl radical containing 1 to 6 carbon atoms, an alkenyl radical containing 2 to 6 carbon atoms, a cycloalkyl radical containing 3 to 6 carbon atoms, a phenyl radical unsubstituted or substituted with one or more identical or different atoms or radicals selected from halogen atoms, alkyl, alkoxy, dialkylamino, acylamino, alkoxycarbonylamino, trifluoromethyl, 2-furyl, 3-furyl, 2-thienyl, 3-thienyl, 2-thiazolyl, 4-thiazolyl, or 5-thiazolyl radicals, and $R_4$ represents a hydroxyl radical, an unbranched or branched alkoxy radical containing 1 to 6 carbon atoms, or an unbranched or branched alkanoyloxy radical containing 1 to 6 carbon atoms.

3. A taxoid according to claim 1 wherein Z represents a hydrogen atom or a radical of general formula (II) in which $R_1$ represents a benzoyl radical or a radical $R_2$—O—CO— in which $R_2$ represents a tert-butyl radical and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical, and $R_4$ represents a hydroxyl, methoxy or acetoxy radical.

4. A process for preparing a taxoid according to claim 1, said process comprising heating a product of general formula (III):

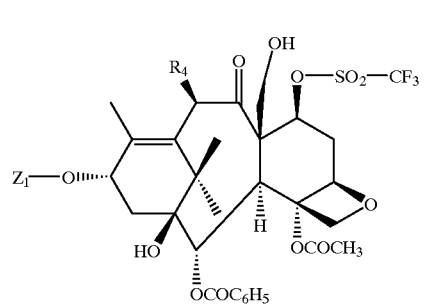

in which $R_4$ is defined as above and $Z_1$ represents a hydrogen atom or a radical of general formula:

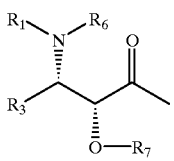

(IV)

in which either $R_6$ represents a hydrogen atom and $R_7$ represents a hydrogen atom or a group protecting the hydroxyl function, or $R_6$ and $R_7$ together form a saturated 5- or 6-membered heterocycle, in the presence of an activating agent to obtain a product of general formula:

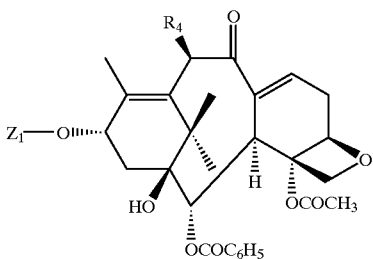

(V)

in which $Z_1$ and $R_4$ are defined as above, followed, where appropriate, by replacement of the protective groups by hydrogen atoms.

5. The process according to claim 3, wherein the process is performed in an organic solvent selected from ethers, nitriles, or mixtures thereof, at a temperature between 20° C. and the refluxing temperature of the reaction mixture.

6. The process according to claim 5, wherein the protective groups $R_7$ and/or $R_6$ and $R_7$ are replaced by hydrogen atoms, in the following manner:

(1) when $R_6$ represents a hydrogen atom and $R_7$ represents a group protecting the hydroxyl function, the protective groups are replaced by hydrogen atoms (a) by means of an inorganic or organic acid or mixtures thereof, in an organic solvent selected from alcohols, ethers, esters, aliphatic hydrocarbons, halogenated aliphatic hydrocarbons, aromatic hydrocarbons or nitriles at a temperature ranging from −10 to 60° C., (b) by means of a source of fluoride ions, or (c) by catalytic hydrogenation, (2) when $R_6$ and $R_7$ together form a saturated 5- or 6-membered heterocycle, and more especially an oxazolidine ring of general formula:

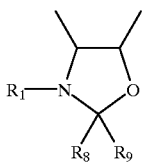

(VI)

in which $R_1$ is defined as above and $R_8$ and $R_9$, which may be identical or different, represent a hydrogen atom, an alkyl radical containing 1 to 4 carbon atoms, or an aralkyl radical in which the alkyl portion contains 1 to 4 carbon atoms and the aryl portion represents a phenyl radical unsubstituted or substituted with one or more alkoxy radicals containing 1 to 4 carbon atoms, or an aryl radical representing a phenyl radical unsubstituted or substituted with one or more alkoxy radicals containing 1 to 4 carbon atoms, or alternatively $R_8$ represents an alkoxy radical containing 1 to 4 carbon atoms or a trihalomethyl radical such as trichloromethyl or a phenyl radical substituted with a trihalomethyl radical such as trichloromethyl and $R_9$ represents a hydrogen atom, or alternatively $R_8$ and $R_9$, together with the carbon atom to which they are linked, form a 4- to 7-membered ring, the protective group formed by $R_6$ and $R_7$ is replaced by hydrogen atoms, in the following manner:

(a) when $R_1$ represents a tert-butoxycarbonyl radical and $R_8$ and $R_9$, which may be identical or different, represent an alkyl radical or an aralkyl or aryl radical, or alternatively $R_8$ represents a trihalomethyl radical or a phenyl radical substituted with a trihalomethyl radical and $R_9$ represents a hydrogen atom, or alternatively $R_8$ and $R_9$ together form a 4- to 7-membered ring, the ester of general formula (V) is treated with an inorganic or organic acid, where appropriate in an organic solvent, to obtain the product of general formula:

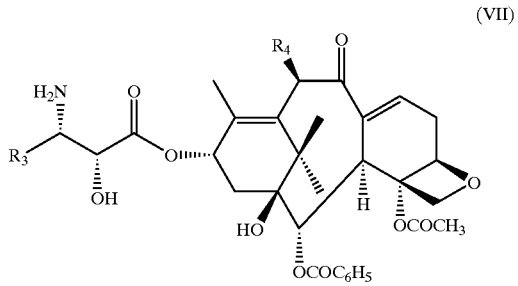

(VII)

in which $R_3$ and $R_4$ are defined as above, which is acylated by means of benzoyl chloride in which the phenyl ring is unsubstituted or substituted or by means of thenoyl chloride, furoyl chloride or of a product of general formula (VIII):

$$R_2\text{—O—CO—X} \quad \text{(VIII)}$$

in which $R_2$ is defined as above and X represents a halogen atom or a residue —O—$R_2$ or —O—CO—O—$R_2$, to obtain a product of general formula (I) in which Z represents a radical of general formula (II), (b) when $R_1$ represents an unsubstituted or substituted benzoyl radical, a thenoyl or furoyl radical or a radical $R_2$O—CO— in which $R_2$ is defined as above, $R_8$ represents a hydrogen atom or an alkoxy radical containing 1 to 4 carbon atoms or a phenyl radical substituted with one or more alkoxy radicals containing 1 to 4 carbon atoms and $R_9$ represents a hydrogen atom, the protective group formed by $R_6$ and $R_7$ is replaced by hydrogen atoms, in the presence of an inorganic or organic acid or mixtures thereof in a stoichiometric or catalytic amount, in an organic solvent selected from alcohols, ethers, esters, aliphatic hydrocarbons, halogenated aliphatic hydrocarbons and aromatic hydrocarbons at a temperature of between −10 and 60° C.

7. A pharmaceutical composition, comprising at least one taxoid according to claim 1 wherein Z represents a radical of general formula (II), in combination with one or more pharmaceutically acceptable diluents or adjuvants and optionally one or more compatible and pharmacologically active compounds.

8. The taxoid of claim 1, wherein, in the definition of $R_2$, the 5-membered aromatic heterocyclic radical is selected from furyl or thienyl radicals.

9. The taxoid of claim 2, wherein said phenyl radical is substituted with fluorine or chlorine.

10. The taxoid of claim 2, wherein said phenyl radical is substituted with a methyl radical.

11. The taxoid of claim 2, wherein said phenyl radical is substituted with a methoxy radical.

12. The taxoid of claim 2, wherein said phenyl radical is substituted with a dimethylamino radical.

13. The taxoid of claim 2, wherein said phenyl radical is substituted with an acetylamino radical.

14. The taxoid of claim 2, wherein said phenyl radical is substituted with a tert-butoxycarbonylamino radical.

15. The process of claim 4, wherein said activating agent is selected from alkali metal halides, alkali metal azides, ammonium salts or salts of silica.

* * * * *